United States Patent
Condie et al.

(10) Patent No.: US 9,182,364 B1
(45) Date of Patent: Nov. 10, 2015

(54) HOT WIRE NEEDLE PROBE FOR THERMAL CONDUCTIVITY DETECTION

(71) Applicants: Keith Glenn Condie, Idaho Falls, ID (US); Joy Lynn Rempe, Idaho Falls, ID (US); Darrell Lee Knudson, Firth, ID (US); Joshua Earl Daw, Idaho Falls, ID (US); Steven Curtis Wilkins, Idaho Falls, ID (US); Brandon S Fox, Ferron, UT (US); Ban Heng, Logan, UT (US)

(72) Inventors: Keith Glenn Condie, Idaho Falls, ID (US); Joy Lynn Rempe, Idaho Falls, ID (US); Darrell Lee Knudson, Firth, ID (US); Joshua Earl Daw, Idaho Falls, ID (US); Steven Curtis Wilkins, Idaho Falls, ID (US); Brandon S Fox, Ferron, UT (US); Ban Heng, Logan, UT (US)

(73) Assignee: U.S. Department of Energy, Washington, DC (US)

( * ) Notice: Subject to any disclaimer, the term of this patent is extended or adjusted under 35 U.S.C. 154(b) by 507 days.

(21) Appl. No.: 13/648,502

(22) Filed: Oct. 10, 2012

(51) Int. Cl.
*G01N 25/18* (2006.01)
*G01N 30/66* (2006.01)

(52) U.S. Cl.
CPC .............. *G01N 25/18* (2013.01); *G01N 30/66* (2013.01)

(58) Field of Classification Search
CPC .............................. G01N 30/66; G01N 25/18
USPC .......... 374/44–45, 163, 164, 29, 30, 137, 208
See application file for complete search history.

(56) References Cited

U.S. PATENT DOCUMENTS

| | | | | | |
|---|---|---|---|---|---|
| 1,435,392 | A | * | 11/1922 | Heiser | 219/552 |
| 3,279,239 | A | * | 10/1966 | Arends et al. | 374/44 |
| 3,592,060 | A | * | 7/1971 | Laverman | G01N 25/18 374/43 |
| 3,832,524 | A | * | 8/1974 | Takiguchi | 219/216 |
| 4,344,315 | A | * | 8/1982 | Moxon | G01N 33/381 374/44 |
| 4,453,835 | A | * | 6/1984 | Clawson et al. | 374/185 |
| 4,861,167 | A | * | 8/1989 | Lobo et al. | 374/44 |
| 5,881,117 | A | * | 3/1999 | Matteson | G01F 23/247 376/258 |
| 6,097,009 | A | * | 8/2000 | Cole | 219/528 |
| 7,670,046 | B2 | * | 3/2010 | Mitov | G01N 25/18 374/29 |
| 7,871,198 | B2 | | 1/2011 | Rempe et al. | |
| 8,156,632 | B2 | * | 4/2012 | Mahajan et al. | 29/595 |
| 2008/0175299 | A1 | * | 7/2008 | Mahajan et al. | 374/44 |
| 2008/0205483 | A1 | | 8/2008 | Rempe et al. | |
| 2008/0310477 | A1 | * | 12/2008 | Mitov | 374/44 |

FOREIGN PATENT DOCUMENTS

DE          10012938 A1 * 10/2001

* cited by examiner

*Primary Examiner* — Gail Kaplan Verbitsky
(74) *Attorney, Agent, or Firm* — Michael J. Dobbs; Felisa L. Leisinger; John T. Lucas

(57) ABSTRACT

An apparatus comprising a needle probe comprising a sheath, a heating element, a temperature sensor, and electrical insulation that allows thermal conductivity to be measured in extreme environments, such as in high-temperature irradiation testing. The heating element is contained within the sheath and is electrically conductive. In an embodiment, the heating element is a wire capable of being joule heated when an electrical current is applied. The temperature sensor is contained within the sheath, electrically insulated from the heating element and the sheath. The electrical insulation electrically insulates the sheath, heating element and temperature sensor. The electrical insulation fills the sheath having electrical resistance capable of preventing electrical conduction between the sheath, heating element, and temperature sensor. The control system is connected to the heating element and the temperature sensor.

18 Claims, 2 Drawing Sheets

HOT WIRE NEEDLE PROBE FOR THERMAL CONDUCTIVITY DETECTION

GOVERNMENT INTERESTS

The United States Government has rights in this invention pursuant to Contract No. DE-AC07-05-ID14517, between the U.S. Department of Energy (DOE) and Battelle Energy Alliance.

FIELD OF THE INVENTION

The present invention relates to an apparatus for measuring thermal conductivity, preferably for the in-pile measurement of thermal conductivity of nuclear materials.

BACKGROUND OF THE INVENTION

Current techniques for measuring thermophysical properties, particularly thermal conductivity, in high-temperature, in-pile applications are both slow and inaccurate. For instance, thermophysical properties must be known before new fuel compositions and structural materials are deployed in nuclear reactors. Thermal conductivity is one of the most important properties for predicting fuel and material performance, and is highly dependent on physical structure, chemical composition, and state of matter. During irradiation, the physical structure and chemical composition of nuclear fuels and components change as a function of time and position within the reactor.

Measurement of thermal conductivity of nuclear fuels and materials is currently primarily done in "hot cells." In these cells, previously-irradiated samples are removed from their environment for testing. This technique has several disadvantages: it is expensive and time consuming to repeatedly remove and return samples to the in-pile testing environment, the process may disturb the physical properties of the sample, and this method can only provide a snapshot of the sample's physical properties at the end state when the measurement is made.

Currently, a thermocouple approach is the only technique used to detect thermal conductivity in high-temperature reactor applications (i.e. in-pile testing of nuclear fuel). Typically this approach uses thermocouples inserted into the interior and exterior of a sample. This approach assumes several conditions about the sample: uniform composition, uniform density, minimal gap conductance effects, and uniform heat generation. Additionally, this method of testing requires specially designed samples to minimize these factors. Hence, the current approach requires specialized (non-prototypical) samples and is susceptible to high levels of uncertainty due to the assumptions made. Therefore, a need for an accurate way of measuring thermal conductivity without removing samples is needed.

Additionally, in nuclear applications, transmutation of elements can alter the performance of probe materials as well as potentially cause damage to probe components. For example, tungsten and rhenium thermocouples can be decalibrated by transmutation in-pile. Thus, there is a significant need for probes with both temperature and radiation resistance.

SUMMARY OF THE INVENTION

An apparatus for the measurement of thermal conductivity. The apparatus comprises a needle probe and a control system. The control system comprises a voltage detector and a voltage supply. The needle probe comprises a sheath, a heating element, a temperature sensor, and an electrical insulator. The sheath must have a melting temperature greater than the operating temperature of the heating element. In one embodiment, the sheath has two diameters whereby the first diameter is smaller than the second. The voltage detector is electrically connected to the temperature sensor providing a measured voltage across the temperature sensor. The heating element is electrically conductive and contained within the sheath. In an embodiment, the heating element is a wire capable of being joule heated when an electrical current is applied. The temperature sensor is surrounded by the heating element within the sheath. The electrical insulator electrically insulates the sheath, heating element and temperature sensor from each other. The melting temperature of the insulation is higher than the operating temperature of the heating element. Preferably, the insulation has a known thermal conductivity sufficient to avoid heat buildup within the needle probe and avoid obscuring the thermal conductivity of the test sample. The voltage supply is electrically connected to the heating element. Preferably, the insulation, sheath, heating element and temperature sensor each have irradiation resistance sufficient to prevent significant transmutation.

The control system comprises programming capable of relating the measured voltage from the voltage detector to the temperature of the temperature sensor. The programming also comprises a controller for the voltage supplied by the voltage supply. The programming further comprises an algorithm capable of calculating the thermal conductivity from the measured voltage across the temperature sensor.

BRIEF DESCRIPTION OF THE DRAWINGS

Illustrative embodiments of the invention are shown in the drawings.

DETAILED DESCRIPTION OF THE INVENTION

Figure 1:
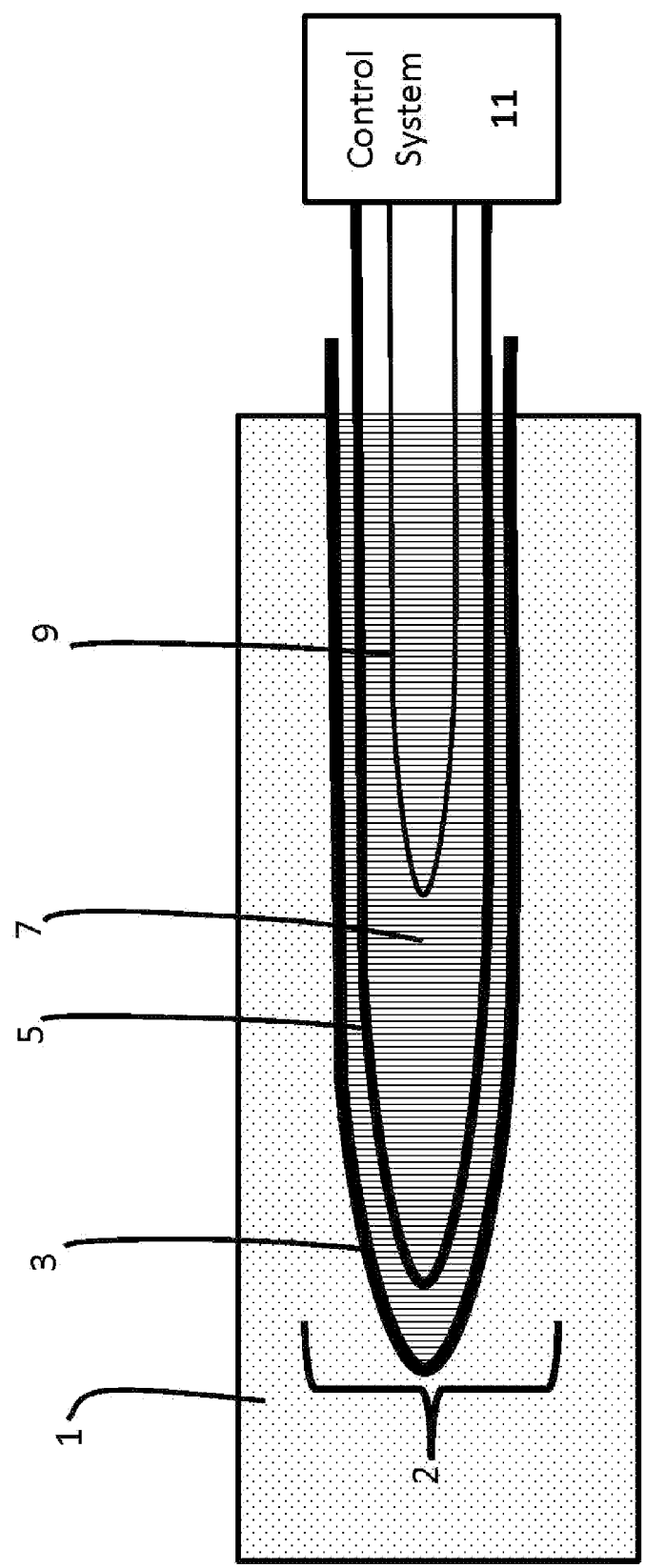
FIG. 1 is a sectional drawing of a hot wire needle probe for thermal conductivity detection including the sheath, a heating element, a temperature sensor, and electrical insulation.

An apparatus for the measurement of thermal conductivity. The apparatus comprises a needle probe and a control system. The control system comprises a voltage detector and a voltage supply. The needle probe comprises a sheath, a heating element, a temperature sensor, and an electrical insulator. The sheath must have a melting temperature greater than the operating temperature of the heating element. In one embodiment, the sheath has two diameters whereby the first diameter is smaller than the second. The voltage detector is electrically connected to the temperature sensor providing a measured voltage across the temperature sensor. The heating element is electrically conductive and contained within the sheath. In an embodiment, the heating element is a wire capable of being joule heated when an electrical current is applied. The temperature sensor is surrounded by the heating element within the sheath. The electrical insulator electrically insulates the sheath, heating element and temperature sensor from each other. The melting temperature of the insulation is higher than the operating temperature of the heating element. Preferably, the insulation has a known thermal conductivity sufficient to avoid heat buildup within the needle probe and not obscuring the thermal conductivity of the test sample. The voltage supply is electrically connected to the heating element. Preferably, the insulation, sheath, heating element and temperature sensor each have irradiation resistance sufficient to prevent significant transmutation.

The control system comprises programming capable of relating the measured voltage from the voltage detector to the temperature of the temperature sensor. The programming also comprises a controller for the voltage supplied by the voltage supply. The programming further comprises an algorithm capable of calculating the thermal conductivity from the measured voltage across the temperature sensor.

One application is in-pile testing of the thermal conductivity of active nuclear fuel. Thus, in one embodiment, a normal application consists of conducting thermal conductivity tests inside of an operating nuclear reactor.

Heating Element

The heating element is an electrical conductor, preferably a wire, capable of joule heating. In one embodiment the heating element is a wire made from material having a neutron thermal absorption cross section low enough to prevent transmutation-induced changes in resistance of the wire. For instance, in one embodiment the heating elements are made of molybdenum doped with one or more of: potassium, silicon, and tungsten. In a preferred embodiment, the molybdenum wire is doped with all three of potassium, silicon, and tungsten.

In one embodiment, the heating element is electrically connected via wires to the voltage supply. In some embodiments the power supplied to the heating element is calculated using the measured current and voltage supplied to the heating element.

In one preferred embodiment the heating element further comprises a low resistance conductor, whereby the heating element comprises a low resistance conductor and a heating conductor. The low resistance conductor is any electrical conductor having an electrical resistance less than the heating conductor. The heating conductor provides the heating as described above for the heating element. The low resistance conductor ensures most of the power is dissipated in the heating element within the probe. Preferably, the electrical connection between the low resistance conductor and heating element is a conical taper, made with tack welds from a laser welder.

Preferably, the low resistance conductor and the heating conductor are both wires and the low resistance conductor has a larger diameter than the heating conductor.

In another embodiment the heating element is electrically connected to at least two pairs of wires. The first pair of wires supplies current to the heating element, and the second pair of wires measures the voltage drop across the heating element.

By way of non-limiting examples, Table 1 contains a list of preferred materials for the heating element and insulation along with respective neutron capture cross sections.

TABLE 1

| Element | Thermal neutron capture crosssection for 2200 m/sec (barns) |
|---|---|
| Beryllium (BeO insulation) | 0.01 |
| Magnesium (MgO insulation) | 0.06 |
| Zirconium | 0.18 |
| Aluminum ($Al_2O_3$ insulation) | 0.23 |
| Niobium | 1.1 |
| Molybdenum | 2.5 |
| Chromium | 2.9 |

TABLE 1-continued

| Element | Thermal neutron capture crosssection for 2200 m/sec (barns) |
|---|---|
| Nickel | 4.6 |
| Tungsten | 19.2 |
| Tantalum | 21.3 |
| Rhenium | 84 |
| Hafnium ($HfO_2$ insulation) | 105 |

Temperature Sensor

The temperature sensor measures the temperature inside the needle probe and comprises a means for transmitting the measurement. Preferably, the temperature sensor is a thermistor or thermocouple applicable in the high temperature and corrosive environment of a nuclear reactor. In a preferred embodiment, the temperature sensor is a thermistor or thermocouple and the temperature is determined by measuring the voltage, which is proportional to the temperature, of the temperature sensor and determining the temperature of the temperature sensor through calibration data.

The temperature sensor is surrounded by the heating element. Preferably, the temperature sensor is completely surrounded by and central to the heating element. By completely surrounding the temperature sensor centrally to the heating element, the heating performed by the heating element is more symmetrical and provides for equal heat dissipation around the temperature sensor. In the alternative, the temperature sensor is partially surrounded by the heating element.

In one application the temperature sensor is a thermocouple. Preferably temperature and radiation resistant during normal operation of the device such that it can measure voltage changes that are proportional to temperature changes. Selection of the appropriate thermocouple and desired properties varies depending on temperatures during operation and the application of the apparatus. In moderately-high temperature applications, the thermocouple is preferably a Type K (chrome/alumel) or a Type N (nicrosil/nisil, nickel-based) thermocouple. For temperatures above 1000° C., an INL-developed molybdenum/niobium alloy High Temperature Irradiation Resistance Thermocouple (HTIR-TC) is recommended. See e.g. Rempe et al. U.S. patent application Ser. No. 11/678,901, hereby incorporated by reference.

Electrical Insulation

The electrical insulator is a material with an electrical resistance capable of preventing electrical interference between the components of the needle probe.

Preferably, in nuclear applications, the electrical insulation has irradiation resistance sufficient to prevent significant transmutation of the electrical insulator. In one embodiment the electrical insulation is comprised of a ceramic insulator. The ceramic insulator is swaged to control its density under changing temperature and radiation conditions, minimize contact between the probe components, and reduce electrical conduction between the components. Preferably, the ceramic insulator is selected from the group of ceramics consisting of alumina ($Al_2O_3$), berillia (BeO), hafnia ($HfO_2$), zirconia ($ZrO_2$), and magnesia (MgO), however in certain applications other ceramic insulators are appropriate.

Sheath

The sheath is a covering capable of containing the elements of the needle probe. Preferably the sheath can protect the contents of the needle probe from external forces including impact and shock.

In one embodiment the sheath comprises a material having a high melting temperature such that it will not melt during operation of the heating element, irradiation resistance sufficient to prevent significant transmutation of the sheath, and chemical stability such that it is resistant to corrosion and material interaction. Materials known to have these qualities include annealed stainless steel and niobium-1% zirconium. In a preferred embodiment the sheath is comprised of stainless steel annealed at 1050° C. or higher, for at least 30 minutes. In some embodiments the material also must be able to be deformed considerably during the fabrication process.

By way of non-limiting examples, Table 2 contains a list of preferred sheath materials and relevant thermal properties.

TABLE 2

| Material | Melting Temperature (° C.) | Maximum Recommended Working Temperature (° C.) |
|---|---|---|
| Molybdenum | 2610 | 1900 |
| Tungsten | 3380 | 2200 |
| Tungsten-5% Rhenium | 3350 | 2300 |
| Molybdenur -50% Rhenium | 2550 | 2200 |
| Niobiurn-1% Zirconium | 2468 | 1800 |
| Tungsten-26% Rhenium | 3120 | 2300 |
| Tantalum | 2996 | 2400 |
| Rhenium | 3180 | 2400 |
| Chromium | 1907 | 1400 (estimated) |
| Nickel | 1453 | 1100 |

Control System

The control system is a device, or set of devices capable of managing, commanding, directing, or regulating the behavior of the apparatus. In at least one embodiment the control system is configured for controlling or measuring signals of voltage, current, and temperature. The control system is capable of recording test time and controlling the voltage provided to the needle probe. Preferably, the control system has a graphical user interface preferably displaying a value related to the temperature at the probe. In one embodiment, the control system has a graphical user interface preferably displaying at least current, voltage, and other iteration variables generated by the control system. The control system is also capable of being calibrated to provide accurate temperature and power measurements for use in calculating thermal conductivity.

Preferably, the control system is an electronic device. In a preferred embodiment, a computer, an ASIC (application specific integrated circuit), a microcontroller, or a combination thereof are used to control the system. In a preferred embodiment, the control system comprises a microcontroller such as the ATMEGA128 as sold by ATMEL.

Preferably, the control system comprises a voltage detector, preferably an analog-to-digital converter (ADC), to measure the voltage across the temperature sensor, preferably a thermocouple. The control system determines a value at least related to the temperature of the temperature sensor from the measured voltage of said voltage detector sensor using the known properties of the temperature sensor. In one embodiment, the determined value at least related to the temperature of the temperature sensor is simply the voltage across the temperature sensor as measured by an ADC.

The control system preferably comprises a voltage supply to adjust the voltage across the heating element. In one embodiment, the control system comprises an digital-to-analog converter (ADC) thereby providing a known voltage to the heating element.

Preferably, the control system has memory storage capable of storing a loop count, program pointer, as well as various registers and an arithmetic control unit capable of performing mathematical functions. Preferably, flash memory, hard disk, or other storage media is used to store a computer program performing the various calculations and controls of the needle probe.

In a preferred embodiment the control system calculates the thermal conductivity, k, of the sample using the following relation.

$$k = \frac{Q_w \ln\left(\frac{t_2 - t_0}{t_1 - t_0}\right)}{4\pi(T_2 - T_1)}$$

Where the time between $t_1$ and $t_2$ is the time period corresponding to where the plot of temperature against the natural log of time is linear. Where the power per unit length (W/m) of the heater wire, $Q_w$, is related to the thermocouple temperature at the time when the linear portion of the curve started, $T_1$, and the temperature when the linear portion of the response curve ended, $T_2$. References include a time correction factor, $t_0$, calculated from the data to account for the finite size of the heater and differences in properties between the sample, line heater, and thermocouple.

In one embodiment the thermal conductivity of the sample is calculated using the relation described from the ASTM needle probe testing standard. See ASTM D 5334-08. "Standard Test Method for Determination of Thermal Conductivity of Soil and Soft Rock by the Thermal Needle Probe Procedure", Approved 2008, hereby incorporated by reference.

$$k = C\frac{VI}{4\pi SL}$$

Where: k is the thermal conductivity of the sample, C is a calibration factor, V is the voltage applied to the probe, I is the current through the probe, S is the average slope of the linear segment of the temperature response, L is the length of the heater section.

Preferred Embodiments

In at least one embodiment the heating element is a wire made from material having a neutron thermal absorption cross section low enough to prevent transmutation-induced changes in resistance of the wire. Additionally, in said embodiments, the heating element is electrically connected to a low resistance conductor electrically connected to the control system. The low resistance conductor has lower electrical resistance than the heating element, whereby the power supplied to the heating element can be derived from the measured current and voltage supplied to the heating element. Furthermore, the temperature sensor is a thermocouple sufficiently temperature and radiation resistant to measure changes in voltage proportional to the temperature. The electrical insulation is a ceramic insulator. The sheath comprises a material having a melting temperature such that it will not melt during operation of the heating element, irradiation resistance sufficient to prevent transmutation of the sheath, and chemical stability such that it is significantly resistant to corrosion and material interaction. The control system controls signals of voltage, current, and temperature. The control system is also capable of recording test time and controlling voltage supplied to the needle probe and heating element. It also provides accurate temperature and power measurements used in calculating thermal conductivity.

In a preferred embodiment, the heater element comprises molybdenum doped with at least one of potassium, silicon, and tungsten. In addition, the thermocouple comprises one of a Type K (chrome/alumel), Type N (nicrosil/nisil), or a doped molybdenum/niobium alloy High Temperature Irradiation Resistance thermocouple (HTIR-TC). Additionally, the ceramic insulator is selected from the group consisting of alumina ($Al_2O_3$), berillia (BeO), hafnia ($HfO_2$), zirconia ($ZrO_2$), and magnesia (MgO). In the preferred embodiment the sheath comprises annealed stainless steel or niobium 1% zirconium alloy.

In another embodiment the apparatus is adapted for in-pile (nuclear reactor) applications. The apparatus is constructed using special fabrication techniques including swaging a small tube over two wire tips to avoid embrittlement of the junction in a high-temperature-irradiation-resistant thermocouple. In this application normal operation includes testing in conventional and material test reactors (MTRs). Some MTRs may have a power rating over 250 $MW_{th}$, and a thermal neutron flux of $1 \times 10^{15}$ $n/cm^2$-s, however operation of MTRs also includes lower ratings for power and neutron flux levels. Irradiation tests evaluate a range of fuel types comprising ceramic fuels, preferably including oxide, nitride, and carbide; and/or metallic fuels. In at least one embodiment, during normal operation, the probe may experience temperatures of over 1,800° C., some embodiments of the apparatus have lower recommended working temperatures.

In one embodiment, the apparatus was tested in a 600° C. furnace for over 1000 hours and 700° C. for an additional 100 hours. These tests showed fewer than 5% error in temperature monitoring and thermal conductivity measurement during the duration of the test. In other embodiments higher error levels may be acceptable under other testing conditions.

In one embodiment, the apparatus comprises a Type K thermocouple, a Chromel heater and Chromel wires, MgO insulation, a Nb-1% Zr sheath, approximately 0.010 in diameter thermocouple wire, approximately 0.010 in diameter heater wire, approximately 0.010 in diameter lead wires, the probe being approximately 0.095 in diameter and approximately 4.0 inch length.

In one embodiment, the apparatus comprises a Type K thermocouple, a KW—Mo heater and Chromel wires, MgO insulation, a Nb-1% Zr sheath, approximately 0.010 inch diameter thermocouple wire, approximately 0.010 in diameter heater wire, approximately 0.020 inch diameter lead wires, the probe being approximately 0.095 in diameter and approximately 5.56 inch length.

In one embodiment, the apparatus comprises a Type K thermocouple, a Chromel heater and Chromel wires, MgO insulation, a Nb-1% Zr sheath, approximately 0.010 in diameter thermocouple wire, less than 0.01 in diameter heater wire, approximately 0.015 in diameter lead wires, the probe being approximately 0.095 in diameter and approximately 7.375 in length.

In at least one embodiment probes have been constructed using alumina insulation, nickel heater lead wires, Type-K thermocouples, and stainless steel sheaths.

FIG. 1

FIG. 1 is a sectional drawing of hot wire needle probe 2 for thermal conductivity detection comprising the sheath 3, a heating element 5, electrical insulation 7, a temperature sensor 9, and a control system 11 as described above. As shown, a testing material 1 is tested by contact with a probe 2 comprising a sheath 3, a heating element 5, insulation 7, and a temperature sensor 9. The control system 11, as described above is connected to the heating element 5 and the temperature sensor 9. The sheath 3 encompasses the heating element 5, insulation 7, and a temperature sensor 9 of the needle probe. The insulation 7 electrically and physically separates the sheath 3, heating element 5, and temperature sensor 9. In this embodiment the heating element 5 is substantially centered within the interior surface of the sheath 3, and forms a U-Shape substantially parallel to the interior surface of the sheath 3. Additionally, the temperature sensor 9 is positioned near the center of the needle probe such that it can measure changes in the temperature of the needle probe necessary for calculating changes in thermal conductivity in the testing material. A centered temperature sensor 9 in relationship to the heating element 5 is preferred the temperature sensor 9 will be equally affected by either side of the heating element 5.

FIG. 2

Figure 2:
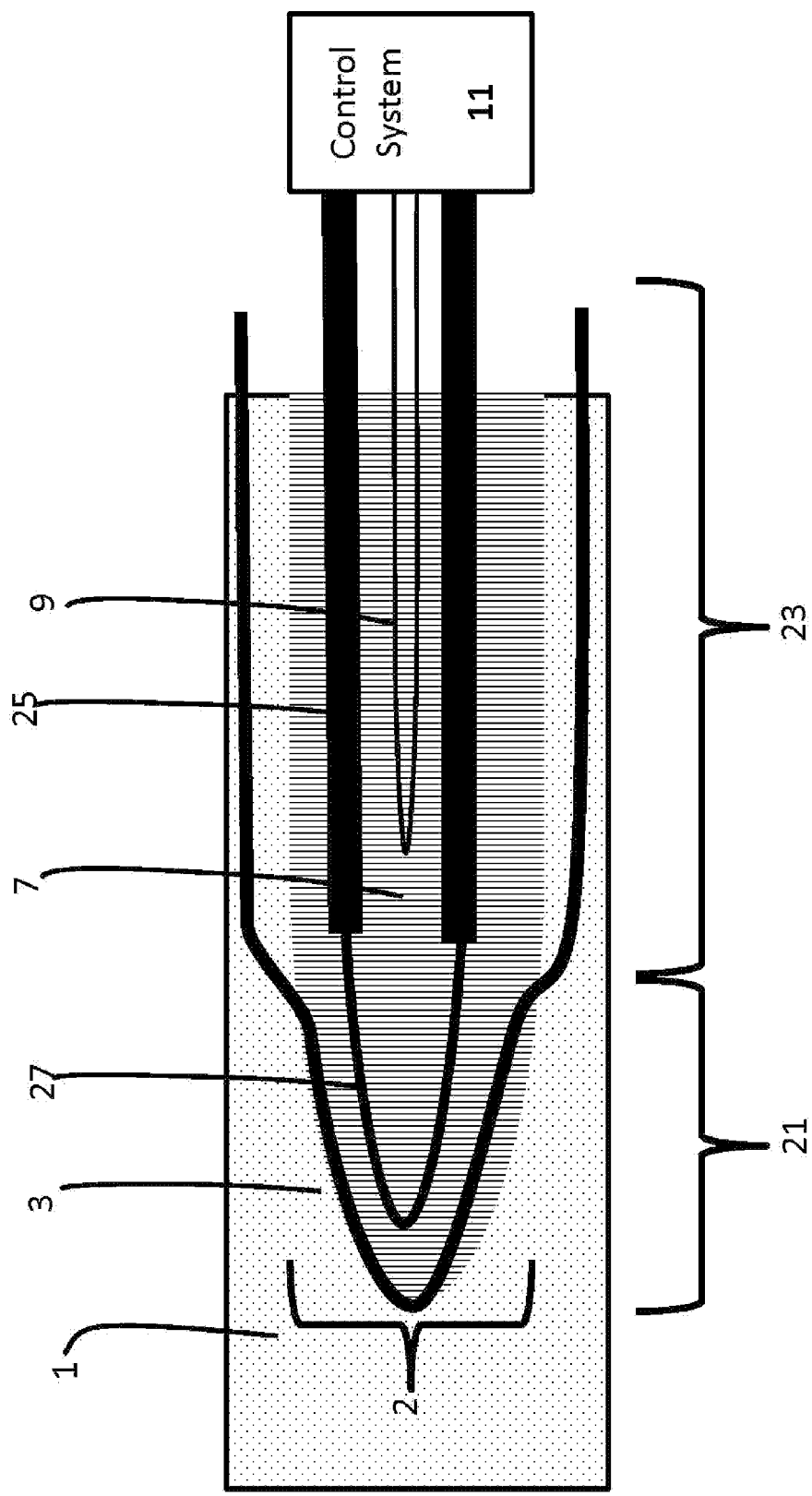
FIG. 2 is a sectional drawing of a preferred embodiment of the apparatus illustrative of large diameter wires attached to a heating element.

FIG. 2 is a sectional drawing of a preferred embodiment of the apparatus illustrative of large diameter wires attached to a heating element. The embodiment shown in FIG. 2 is as described in FIG. 1 except for the sheath 3 having a smaller diameter portion 21 and larger diameter portion 23 and the heating element 5 comprising a low resistance conductor 25 and a heating conductor 27 as described above.

The sheath 3 is one continuous piece having a larger diameter 23 nearer the posterior end of the needle probe 2 and forming into a small diameter 21 at the tip of the needle probe 2.

The low resistance conductor 25 is electrically connected to the control system 11 and forms one continuous piece electrically connected in series with the heating conductor 27. Preferably, the interface between the low resistance conductor 25 and the heating conductor 27 are bonded via a weld. The heating conductor 27 follows the inner side of the smaller diameter portion 21 of the sheath 3 and is electrically connected to the low resistance conductor 25 along the inner side of the larger diameter portion 23. The low resistance conductor 25 can have a larger diameter than the wire and are preferably electrically connected to the wire using tack welds and tapering.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

All publications and patent documents cited in this application are incorporated by reference in their entirety for all purposes to the same extent as if each individual publication or patent document were so individually denoted.

Any element in a claim that does not explicitly state "means for" performing a specified function, or "step for" performing a specific function, is not to be interpreted as a "means" or "step" clause as specified in 35 U.S.C. §112, ¶6. In particular, the use of "step of" in the claims herein is not intended to invoke the provisions of 35 U.S.C. §112, ¶6.

The embodiment of the invention in which an exclusive property or privilege is claimed is defined as follows:

1. An apparatus for the measurement of the thermal conductivity comprising:
   a) a control system, and a needle probe;
   b) said control system comprising a voltage detector, and a voltage supply;
   c) said needle probe comprising a sheath, a heating element, a temperature sensor, and an electrical insulator;
   d) said sheath comprising a melting temperature greater than the operating temperature of the heating element;
   e) said voltage detector electrically connected to said temperature sensor providing a measured voltage related to the temperature of said temperature sensor;
   f) said heating element electrically conductive and contained within said sheath;
   g) said temperature sensor surrounded by said heating element within said sheath;
   h) said electrical insulator electrically insulating said sheath, said heating element and said temperature sensor from each other;
   i) said electrical insulator comprising a melting temperature greater than the operating temperature of the heating element;
   j) said voltage control supply electrically connected to said heating element;
   k) said control system comprising programming comprising:
      i) determining a value at least related to the temperature of said temperature sensor from said measured voltage of said voltage detector;
      ii) controlling the voltage supplied by the voltage supply; and
      iii) calculating the thermal conductivity from said measured voltage across said temperature sensor.

2. The apparatus as claimed in claim 1 wherein:
   a) said heating element comprises molybdenum doped with at least one of: potassium, silicon, and tungsten.

3. The apparatus as claimed in claim 1 wherein:
   a) said heating element comprises a low resistance conductor electrically connected in series with a heating conductor forming one continuous piece;
   b) said low resistance conductor having lower electrical resistance than said heating conductor; and
   c) said low resistance conductor electrically connected to said control system.

4. The apparatus as claimed in claim 3 wherein:
   a) said heating conductor is a wire;
   b) said low resistance conductor is a wire have a larger diameter than said heating conductor; and
   c) said electrical connection of said heating element comprises a conical taper.

5. The apparatus as claimed in claim 1 wherein:
   a) said temperature sensor is a thermocouple.

6. The apparatus as claimed in claim 5 wherein:
   a) said thermocouple comprises a Type K (chrome/alumel) Type N (nicrosil/nisil) thermocouple, or a doped molybdenum/niobium alloy High Temperature Irradiation Resistance Thermocouple (HTIR-TC).

7. The apparatus as claimed in claim 1 wherein:
   a) said electrical insulator comprises a ceramic insulator.

8. The apparatus as claimed in claim 7 wherein:
   a) said electrical insulator is selected from the group consisting of alumina ($Al_2O_3$), berillia (BeO), hafnia ($HfO_2$), zirconia ($ZrO_2$), and magnesia (MgO).

9. The apparatus as claimed in claim 1 wherein:
   a) said sheath comprises annealed stainless steel or Niobium-1% Zirconium.

10. The apparatus as claimed in claim 1 wherein:
    a) said sheath is coated with thermally conductive grease.

11. The apparatus as claimed in claim 1 wherein said programming comprises:
    a) calculating the thermal conductivity, k, using the following equation;

$$k = \frac{Q_w \ln\left(\frac{t_2 - t_0}{t_1 - t_0}\right)}{4\pi(T_2 - T_1)}$$

b) wherein the time between $t_1$ and $t_2$ is the time period corresponding to where the plot of temperature against the natural log of time is linear and $Q_w$ is related to the temperature sensor temperature at the time $T_1$, and the temperature when the linear portion of the response curve ended, $T_2$, derived from said measured voltage across said temperature sensor.

12. The apparatus as claimed in claim 4 wherein said programming comprises:
    an algorithm capable of calculating the thermal conductivity, k, using the following equation;

$$k = C\frac{VI}{4\pi SL}$$

wherein k is the thermal conductivity of the sample, C is a calibration factor, V is the voltage applied to the heating element, I is the current applied to the heating element, S is the average slope of the linear segment of the temperature of the temperature sensor derived from said measured voltage across said temperature sensor, and L is the length of said heater conductor.

13. The apparatus as claimed in claim 1 wherein said temperature sensor is completely surrounded by and central to said heating element.

14. The apparatus as claimed in claim 3 wherein:
    a) said heating conductor is a wire;
    b) said low resistance conductor is a wire have a larger diameter than said heating conductor;
    c) said temperature sensor is completely surrounded by and central to said heating element;
    d) said electrical connection of said heating element comprises a conical taper; and
    e) said temperature sensor is a thermocouple.

15. The apparatus as claimed in claim 14 wherein:
    a) said heating element comprises molybdenum doped with at least one of: potassium, silicon, and tungsten;
    b) said thermocouple comprises a Type K (chrome/alumel) Type N (nicrosil/nisil) thermocouple, or a doped molybdenum/niobium alloy High Temperature Irradiation Resistance Thermocouple (HTIR-TC);
    c) said electrical insulator is selected from the group consisting of alumina ($Al_2O_3$), berillia (BeO), hafnia ($HfO_2$), zirconia ($ZrO_2$), and magnesia (MgO);
    d) said sheath comprises annealed stainless steel or Niobium-1% Zirconium; and
    e) said sheath is coated with thermally conductive grease.

16. The apparatus as claimed in claim 15 wherein said programming comprises:
  a) calculating the thermal conductivity, k, using the following relation;

$$k = \frac{Q_w \ln\left(\frac{t_2 - t_0}{t_1 - t_0}\right)}{4\pi(T_2 - T_1)}$$

b) wherein the time between $t_1$ and $t_2$ is the time period corresponding to where the plot of temperature against the natural log of time is linear and $Q_w$ is related to the temperature sensor temperature at the time $T_1$, and the temperature when the linear portion of the response curve ended, $T_2$, derived from said measured voltage across said temperature sensor.

17. The apparatus as claimed in claim 15 wherein said programming comprises: calculating the thermal conductivity, k, using the following relation;

$$k = C\frac{VI}{4\pi SL}$$

wherein k is the thermal conductivity of the sample, C is a calibration factor, V is the voltage applied to the heating element, I is the current applied to the heating element, S is the average slope of the linear segment of the temperature of the temperature sensor derived from said measured voltage across said temperature sensor, and L is the length of said heater conductor.

18. The apparatus as claimed in claim 1 wherein said temperature sensor is completely surrounded by and central to said heating element.

* * * * *